(12) United States Patent
Hillbratt et al.

(10) Patent No.: US 9,295,836 B2
(45) Date of Patent: Mar. 29, 2016

(54) DIRECTIONALITY DEVICE FOR AUDITORY PROSTHESIS MICROPHONE

(71) Applicants: Martin Evert Gustaf Hillbratt, Mölnlycke (SE); Koen Van den Heuvel, Hove (BE)

(72) Inventors: Martin Evert Gustaf Hillbratt, Mölnlycke (SE); Koen Van den Heuvel, Hove (BE)

(73) Assignee: COCHLEAR LIMITED, Macquarie University, NSW (AU)

(*) Notice: Subject to any disclaimer, the term of this patent is extended or adjusted under 35 U.S.C. 154(b) by 197 days.

(21) Appl. No.: 13/968,873

(22) Filed: Aug. 16, 2013

(65) Prior Publication Data
US 2015/0051439 A1    Feb. 19, 2015

(51) Int. Cl.
*H04R 25/00* (2006.01)
*A61N 1/36* (2006.01)
*G02C 11/06* (2006.01)

(52) U.S. Cl.
CPC ............ *A61N 1/36032* (2013.01); *G02C 11/06* (2013.01); *H04R 25/402* (2013.01); *H04R 25/606* (2013.01)

(58) Field of Classification Search
CPC .... H04R 25/552; H04R 25/60; H04R 25/604; G02C 5/143; G02C 11/06
USPC .......... 381/313, 327, 330, 370, 371, 374, 381
See application file for complete search history.

(56) References Cited

U.S. PATENT DOCUMENTS

| | | | |
|---|---|---|---|
| 4,712,244 A | 12/1987 | Zwicker et al. | |
| 4,773,095 A | 9/1988 | Zwicker et al. | |
| 4,789,044 A | 12/1988 | Akino | |
| 6,021,207 A * | 2/2000 | Puthuff et al. | 381/330 |
| 6,690,807 B1 * | 2/2004 | Meyer | 381/327 |
| 7,031,483 B2 | 4/2006 | Boone et al. | |
| 7,609,842 B2 * | 10/2009 | Sipkema et al. | 381/327 |
| 7,894,621 B2 | 2/2011 | Jensen | |
| 8,139,801 B2 | 3/2012 | Sipkema et al. | |
| 8,891,796 B2 * | 11/2014 | van Halteren | 381/330 |
| 2002/0164041 A1 * | 11/2002 | Zurek | 381/313 |
| 2011/0216927 A1 | 9/2011 | Ball | |

* cited by examiner

*Primary Examiner* — Brian Ensey (57) ABSTRACT

Devices are used to receive sound so as to enhance directionality in a single microphone auditory prosthesis. A tube including a plurality of openings directs sound into a microphone located on the auditory prosthesis. Directionality of such a system is based on a constructive and destructive interference between added sound components as sound enters the openings on the tube. The spacing and size of the openings can be configured such that sounds coming towards the recipient from a predetermined direction are received, while sounds from less desirable directions are cancelled out due to sound wave phase differences.

28 Claims, 11 Drawing Sheets

DIRECTIONALITY DEVICE FOR AUDITORY PROSTHESIS MICROPHONE

BACKGROUND

An auditory prosthesis can be placed behind the ear with support of an ear hook and with optional adhesive. Such prosthesis can include cochlear implants, bone conduction devices, middle ear actuators, inner ear actuators, and acoustic hearing aids. The earhook may be in the form of a tube or other elongate member that extends from the prosthesis to an insert or earmold disposed in the ear canal. Sound received via a microphone in the prosthesis is converted into an output signal and the prosthesis sends a stimulus to the recipient. The type of stimulus depends on the type of prosthesis, for example, cochlear implants provide electrical stimulation and bone conduction devices provide mechanical stimulation.

SUMMARY

Embodiments disclosed herein relate to devices that are used to receive sound at an auditory prosthesis so as to enhance directionality. Such auditory prostheses include, for example, cochlear implants, hearing aids or other types of devices. A tube including a plurality of openings directs sound into a microphone located on the auditory prosthesis. Directionality is based on constructive and destructive interference between added sound components as sound enters the openings on the tube. The openings on the tube result in phase differences in the received sound wave. The spacing and size of the openings can be configured such that sounds coming towards the recipient from a predetermined or desirable direction are received, while sounds from less desirable directions are cancelled out due to sound wave phase differences.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The technologies disclosed herein can be used in conjunction with various types of auditory prostheses, including active transcutaneous bone conduction devices, passive transcutaneous devices, middle ear devices, cochlear implants, and acoustic hearing aids. The devices may be wearable or implantable (either in or on the head, including in specific portions of the anatomy, e.g., in the mouth). Additionally, the technologies may be incorporated into other devices that receive sound and send a corresponding stimulus to a recipient. The corresponding stimulus may be in the form of electrical signals, mechanical vibrations, or acoustical sounds. Examples of such devices are described below. For clarity, however, the devices disclosed herein will be generally described in the context of behind-the-ear auditory prostheses. A microphone tube extends from the microphone inlet to the ear canal, cymba conchae, fossa triangularis, crura of antihelix or scaphoid fossa. In certain embodiments, the tube is located in a forward-facing direction from a behind-the-ear device, either on top of or below the pinna. The microphone tube defines a number of openings that create a directionality pattern which resembles the natural directionality of normal hearing.

Many benefits can be achieved in an auditory prosthesis using the microphone inlet tube configured as described herein. For example, a directionality pattern is achieved with a single microphone, which allows for a smaller device to be designed with half the cost of directionality systems that typically include two microphones spaced apart from each other on the prosthesis. Additionally, unlike a digital solution, such as beam forming, the technology does not require any signal processing and thus will not introduce signal processing artifacts. The disclosed technology can result in higher sound directionality than systems that utilize a hardware directionality microphone with dual microphone inlets. By inserting the tube in the ear canal, cymba conchae, etc., wind noise resistance can also be achieved. Interestingly, the disclosed technologies are not mutually exclusive to the systems described above. Instead, the technologies can be incorporated into known directionality systems (e.g., prosthesis having multiple microphones) to achieve improved performance of auditory prostheses. Certain of those configurations are described below and other configurations will be apparent to a person of skill in the art.

Figure 1:
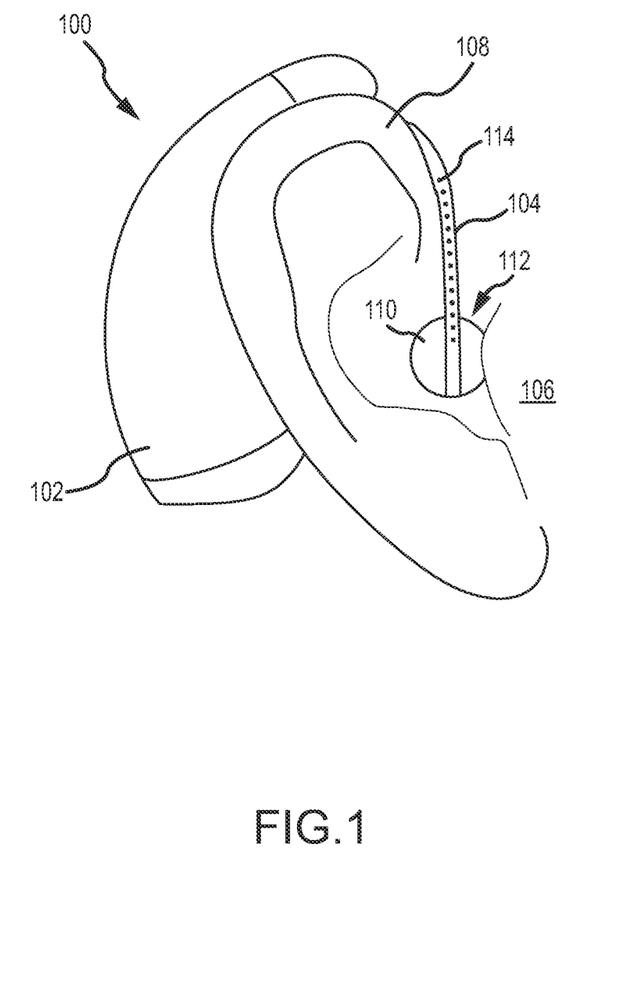
FIG. 1 is a side view of a behind-the-ear auditory prosthesis worn on a recipient.

FIG. 1 depicts an external portion of an auditory prosthesis 100. The auditory prosthesis 100 includes a housing 102 and a tube 104 extending therefrom. Such an auditory prosthesis is often referred to as a "behind-the-ear" device. In other embodiments, the auditory prosthesis may also include a discretely located external portion fixed to a recipient's skull that delivers a stimulus. The tube 104 functions as an ear hook to help secure the auditory prosthesis 100 to a recipient 106. More specifically, the tube 104 wraps around the upper portion of an ear 108 of the recipient 106 and conforms generally to the ear 108 (e.g., the pinna). An insert or earmold 110 is located at a distal end of the tube 104 and is placed within the ear canal 112. The tube 104 defines a plurality of openings 114, which are described in more detail below. In the depicted embodiment, the openings 114 are disposed along an outer surface of the tube 104, relative to the recipient 106. That is, the openings 114 are disposed on the side of the tube 104 opposite the head of the recipient 106. Thus, the openings 114 face away from the side of the head of the recipient 106. In other embodiments, openings can be disposed on a surface of the tube facing forward, that is, towards the face of the recipient. In other embodiments, a tube defining a number of openings may be separate from a discrete earhook that helps locate the auditory prosthesis behind the ear.

Figure 2:
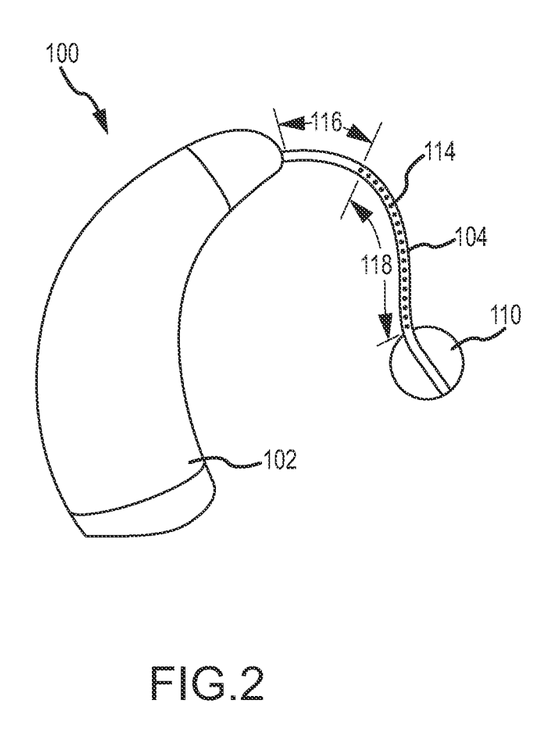
FIG. 2 is a side view of an embodiment of a behind-the-ear auditory prosthesis.

FIG. 2 depicts the auditory prosthesis 100, with the tube 104 extending from the housing 102. A microphone is located within the housing 102 and a microphone inlet extends from an outer surface of the housing 102 to the microphone. The tube 104 is disposed so that an open end thereof is disposed, in embodiments, substantially surrounding the microphone inlet. This allows the sound received via the openings 114 on the tube 104 to be directed into the microphone inlet. The tube 104 includes two discrete portions or lengths, a proximal portion 116 and a distal portion 118. The proximal portion 116 is disposed proximate the housing 102 of the hearing aid 100 and is characterized by an absence of openings. Although the openings 114 can be located along the entire length of the tube 104, utilizing a proximate portion 116 having an absence of openings reduces feedback. Such feedback can occur, for example, when a loudspeaker located in the hearing aid 100 is located too close to the microphone inlet and sound therefrom is received by the microphone, via the openings 114. In embodiments of auditory prostheses that utilize a vibrating stimulation element, such as bone conduction devices, the vibrations can also produce feedback into the microphone. Thus, the proximal portion 116 lacking openings can be desirable in certain embodiments. The distal portion 118 defines a number of openings 114. In general, the distal portion extends from the proximal portion 116 to the insert 110.

Figure 3:
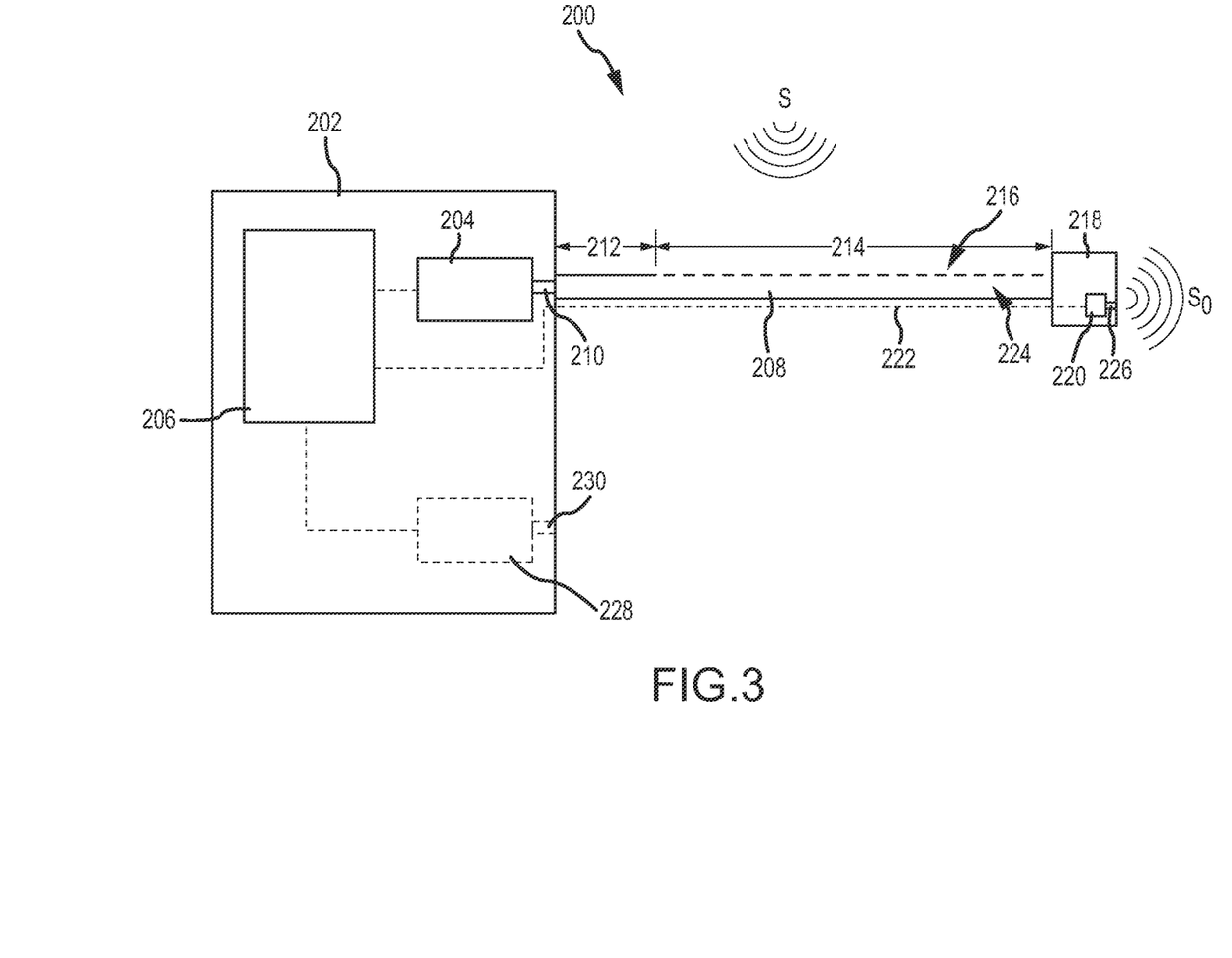
FIG. 3 is a schematic view of an embodiment of an auditory prosthesis.

FIG. 3 is a schematic view of an auditory prosthesis 200, which in this embodiment, is an acoustic hearing aid. The hearing aid 200 includes a housing 202 containing a microphone 204, which can be an omnidirectional microphone, operatively connected to a processor 206. Other types of microphones can be utilized, for example, unidirectional, cardoid, bi-directional, or others. An inlet tube 208 is connected to the housing 202 so as to substantially surround an inlet 210 to the microphone 204. In alternative embodiments, the inlet tube can extend into the housing and terminate at the microphone. As described above, the inlet tube 208 includes a proximal portion 212 and a distal portion 214 defining a plurality of openings 216. The hearing aid 200 also includes an insert or earmold 218 that, in this embodiment, contains a stimulation element, such as a speaker 220, disposed therein. In embodiments, the speaker 220 is operatively connected to the processor 206 via a wire 222 located along an outer surface of the inlet tube 208. In other embodiments, the wire can be embedded in the tube itself, or located within a central lumen 224 of the inlet tube 208.

During use, a sound S passes through the various openings 216 on the inlet tube 208, is transmitted down the central lumen 224 thereof, and is received in the microphone inlet 210. The microphone 204, in turn, sends a signal representative of the received sound to the processor 206, which converts the received sound into an output signal. In embodiments, additional processing of the sound S can be performed by the processor 206 at this time. For example, the processor 206 could eliminate harmful frequencies present in the sound, enhance more desirable frequencies, or perform other signal processing to produce a modified output signal. The output signal is sent from the processor 206 via the wire 222 to the stimulation element 220. The stimulation element 220 sends a stimulus to the hearing device recipient based at least in part on the output. In this case, since the stimulation element 220 is a speaker, the stimulus is an output sound $S_O$, delivered through an outlet 226 in the insert 218. Though not necessary to practice the disclosed technology, the hearing aid 200 depicted in FIG. 3 also can include a second omnidirectional microphone 228. Sound S can be received by this second microphone 228 via a second microphone inlet 230 and an associated signal can be sent to the processor 206. The processor 206 can use beam forming signal processing to convert the received sound S into a desired output signal. It will be apparent, then, that existing auditory prostheses that utilize two microphones and signal processing algorithms can be retrofitted with the microphone inlet tube technology described herein so as to benefit from that technology. Retrofitted prostheses can be programmed with alternative processing algorithms to enable the processor to process the received sounds and produce the desired output signals.

Figure 4:
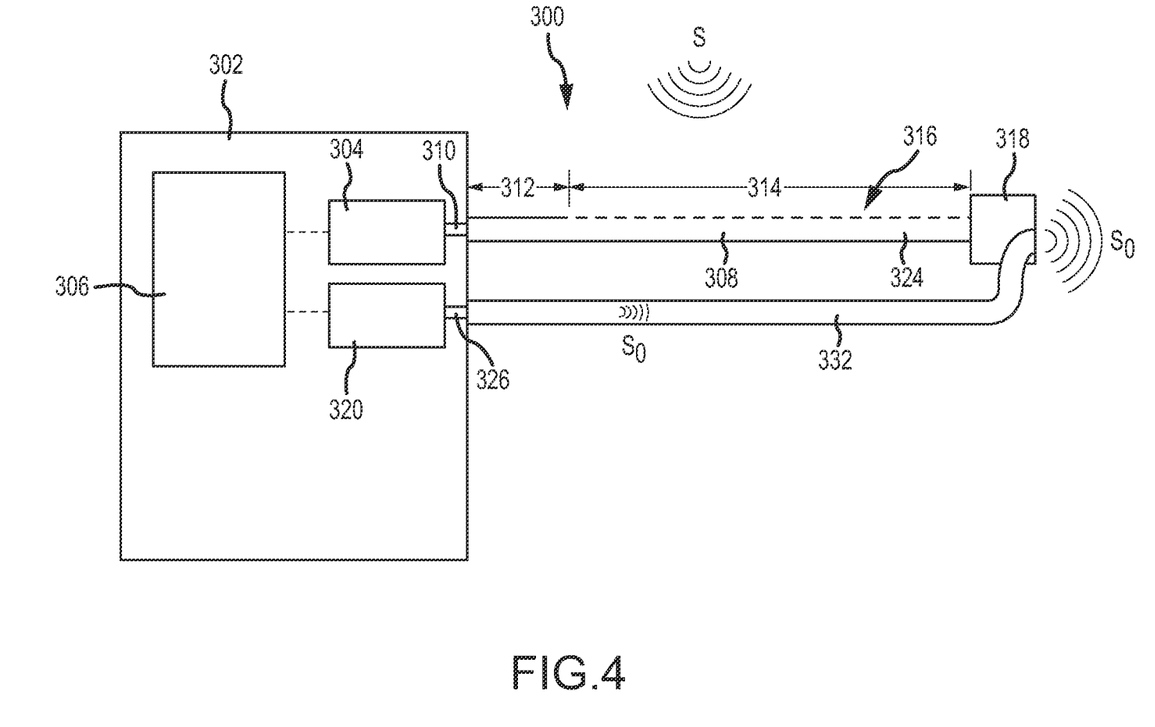
FIG. 4 is a schematic view of another embodiment of an auditory prosthesis.

FIG. 4 is a schematic view of another embodiment of an auditory prosthesis 300, in this case, a hearing aid having a speaker 320 in the housing 302. The housing 302 contains a microphone 304, such as an omnidirectional microphone, operatively connected to a processor 306. An inlet tube 308 is connected to the housing 302 so as to substantially surround an inlet 310 to the microphone 304. In other embodiments, the inlet 310 can be completely surrounded. In alternative embodiments, the inlet tube can extend into the housing and terminate at the microphone. As described above, the inlet tube 308 includes a proximal portion 312 and a distal portion 314 defining a plurality of openings 316. The inlet tube 308 also includes a central lumen 324 and is connected to an insert or earmold 318. Unlike the prosthesis 200 of FIG. 3, the depicted prosthesis 300 includes a stimulation element 320 located within the device housing 302 that is operatively connected to the processor 306. This stimulation element 320 is a speaker that delivers an output sound $S_O$ via a speaker outlet 326 to an outlet tube 332, which can be discrete from or integral with the inlet tube 308. In embodiments, the outlet tube 332 is routed through the insert 318 to deliver the output sound $S_O$ to a recipient. During use, sound S is received by the microphone 304, via the openings 316, can be processed by the processor 306 as described above. Thereafter, the processor 306 sends an output signal to the stimulation element 320. The stimulation element 320 sends an output sound $S_O$, delivered through the outlet tube 332 to and through the insert 318. In further embodiments second omnidirectional microphone, such as that described above with regard to FIG. 3 can be utilized.

Figure 5:
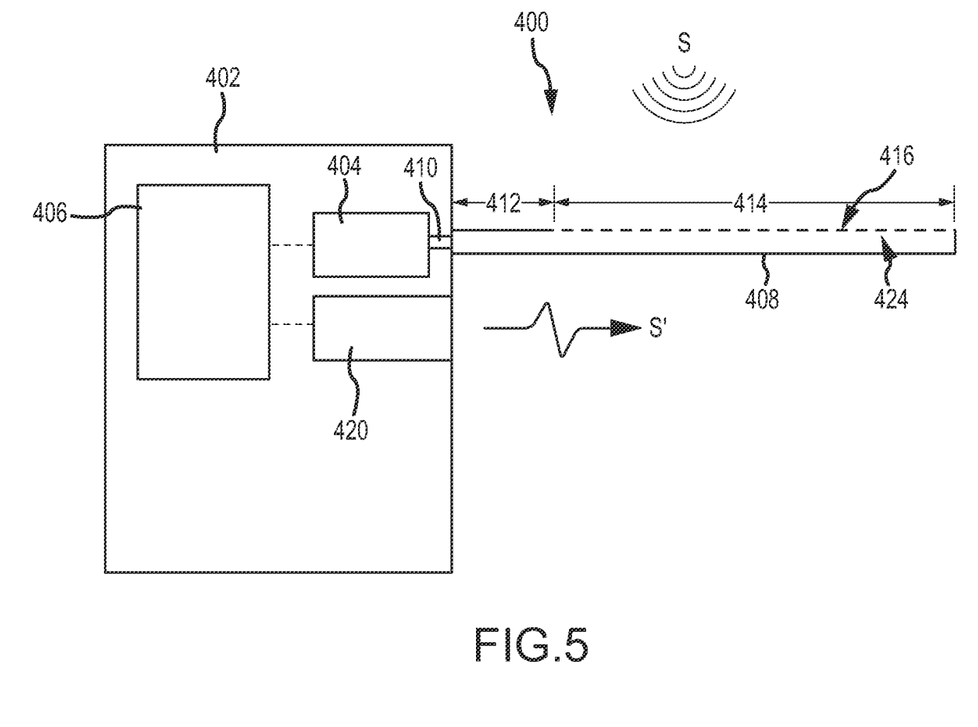
FIG. 5 is a schematic view of another embodiment of an auditory prosthesis.

FIG. 5 is a schematic view of yet another embodiment of an auditory prosthesis 400, which in this case, is a bone conduction device or cochlear implant. The prosthesis 400 includes a housing 402 containing a microphone 404, such as an omnidirectional microphone, operatively connected to a processor 406. An inlet tube 408 is connected to the housing 402 so as to substantially surround an inlet 410 to the microphone 404. In alternative embodiments, the inlet tube can extend into the housing and terminate at the microphone. As described above, the inlet tube 408 includes a proximal portion 412 and a distal portion 414 defining a plurality of openings 416. The inlet tube 408 also includes a central lumen 424. The prosthesis 400 includes a stimulation element 420 located within the device housing 402 that is operatively connected to the processor 406. This stimulation element 420 outputs a stimulus $S_O$ to a recipient, depending on the type of prostheses. In bone conduction devices, the stimulus S' causes a vibration of an implanted device via a vibration element. In cochlear implants, the stimulus S' stimulates the auditory nerve or a portion of the cochlear via an electrode array. In other embodiments, the stimulation element may be located discrete from the housing 402. Other types of stimuli are delivered depending on the type of auditory prosthesis, as known in the art. During use, sound S is received via the openings 416 and microphone 404 and can be processed by the processor 406 as described above. Thereafter, the processor 406 sends an output signal to the stimulation element 420, which in turn send the output stimulus S'. As indicated above, a second omnidirectional microphone can be utilized, but is not required.

Figure 6:
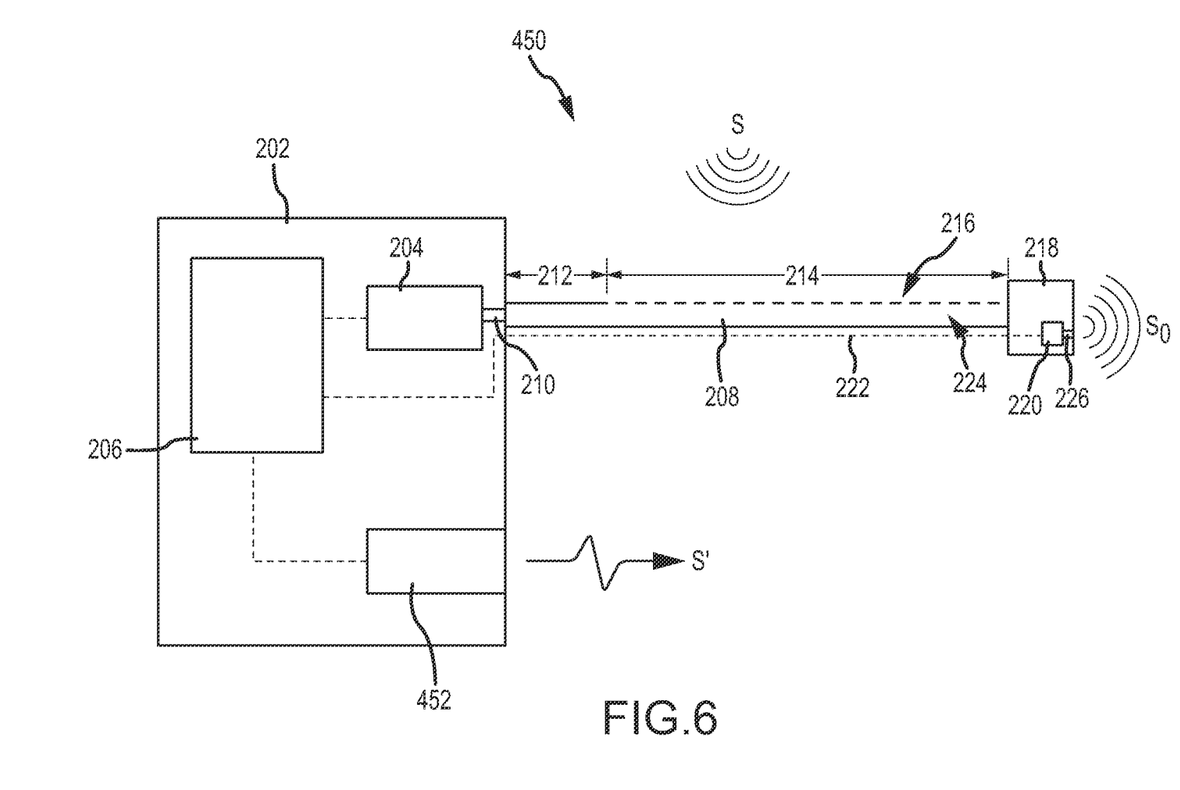
FIG. 6 is a schematic view of another embodiment of an auditory prosthesis.

FIG. 6 depicts yet another embodiment of an auditory prosthesis 450. In this case, the prosthesis 450 is a hybrid device that incorporates two stimulation elements, namely for delivering two different types of stimuli to a recipient. The elements 202-226 are described above with regard to FIG. 3. In general, the stimulus $S_O$ is associated with the lower frequency components of the sound S. Higher frequency components of the sound S are delivered as the stimulus of S' from the second stimulation element 452. As described above, this stimulation element 452 can be a bone conduction device or a cochlear implant. The processor 206 processes the sound S and delivers the appropriate output signals to the two stimulation elements 220, 452. Of course, the stimulation element 452 can be incorporated into the auditory prosthesis 300 of FIG. 4, as can the second omnidirectional microphone 230 depicted in FIG. 3. Additionally, the stimulation elements 420 (FIG. 6) and 462 (FIG. 6) can deliver a stimulus S' via the ear canal (through the insert or earmold) or transcutaneously (for example, via an electrode inserted into the cochlea, as utilized in cochlear implants).

Figure 7A:
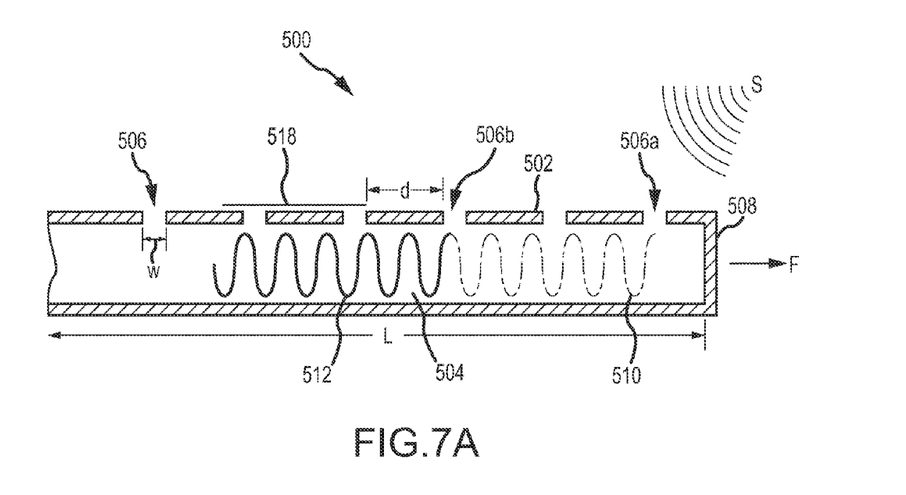
FIGS. 7A and 7B are cross sectional views of embodiments of inlet tubes utilized with an auditory prosthesis.
Figure 7B:
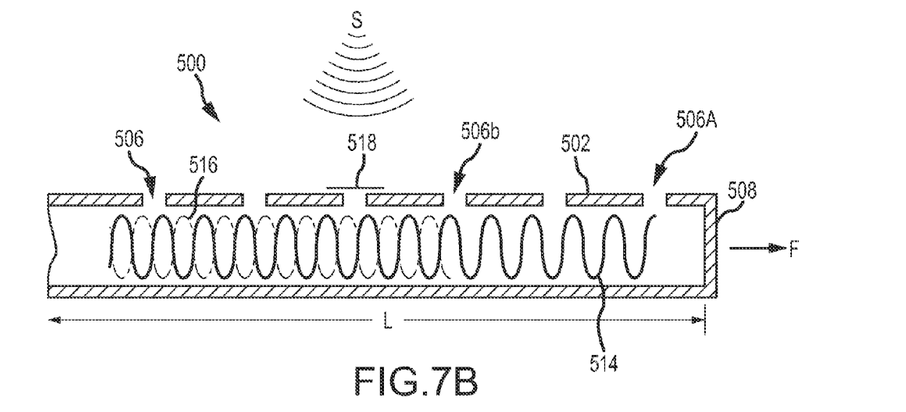

FIGS. 7A and 7B depict top cross sectional views of inlet tubes 500 that can be utilized with the prostheses described herein. Each of FIGS. 7A and 7B depict an inlet tube 500 and sound propagation therein, which is further explained below. The inlet tube 500 is configured as an annular member 502 defining a lumen 504. The annular member 502 also defines a plurality of openings 506 therethrough for receiving a sound S. The lumen 504 defines a cross-sectional area and a length L, which extends from an end 508 of the annular member 502, to a microphone inlet (not shown). Each of the openings 506 defines a width w and adjacent openings are separated by a distance d. Pressure associated with the sound S is added together as the sounds passes through a number of openings 506. The sound S is transmitted through the openings 506 and is constructive or destructive. The sound S is then collected in the microphone at the end of the annular member 502. The separation distance d between the openings 506 along the member 502 acts as delay lines that effect the phase of the sound S as it is transmitted along the lumen 504. The opening 506 width w and separation distance d are optimized such that sounds of certain frequencies remain in phase as they travel down the lumen 504 of the inlet tube 500. Frequencies between about 1 KHz and about 4 KHz are particularly useful, as this is a frequency range generally consistent with speech. Frequencies from about 500 Hz to about 6 KHz are also contemplated. It has been discovered that sounds between about 1 KHz and 4 KHz remain in phase in tubes having openings spaced between about 0.1 mm and about 0.3 mm apart. Additionally, tube openings having widths of about 0.2 mm are also desirable for this frequency range. Of course, other opening widths w and distances d can be utilized. For example, a greater range of frequencies can be received for opening separations of about 0.05 mm to about 0.5 mm. Separations of about 0.2 mm to about 0.4 mm can also be utilized. Larger or smaller width openings can also be utilized, including about 0.3 mm, about 0.4 mm, and up to and exceeding 0.5 mm. Additionally, the opening widths w and separation d need not be uniform along an entire length of tube. The acoustic resistance of the openings can be controlled by using different size openings and by covering one or more of the openings with an acoustically transmissive membrane 518 such as GORTEX or other materials. The membrane 518 also prevents moisture or debris from entering the lumen 504 and causing damage to the associated prosthesis. In certain embodiments, the acoustic resistance can be varied along the length L of the tube. It can be desirable that the resistance through openings closest to the microphone be higher than those farther from the microphone, since sounds propagating the furthest in the tube 500 will be more attenuated. Accordingly, larger openings can be located further from the microphone and the opening size can decrease as distance to the microphone decreases. Separation d along the tube can also vary as required or desired for a particular application.

Returning to FIGS. 7A and 7B, simplified versions of sound S being received in an inlet tube 500 are depicted. Specifically, sound S is depicted as being received only via the openings 506a and 506b. Of course, sounds would be received through all of the openings 506 along the annular member 502. FIG. 7A depicts a condition where the received sounds results in constructive interference between sound waves within the tube 500. Here, the sound S is coming from a direction generally forward F of a device recipient. That is, the sound S direction is consistent with a normal conversation the recipient can be engaged in, or other sounds to which the recipient wishes to direct their attention. As the sound S enters the first opening 506a, a resulting waveform 510 of a particular frequency is transmitted through the lumen 504 toward the microphone. Since the separation distance d and opening width w have been optimized for a typical speech frequency, the sound entering the second opening 506b results in a waveform of an identical frequency, in phase with the waveform 510. The resulting constructive waveform is depicted as bold line 512. This sound is received by the microphone and processed as described above.

FIG. 7B depicts a condition where the received sound results in destructive interference between sound waves within the tube. Here, the sound S is coming from a direction generally to the side of a recipient. Such a sound could be, for example, conversations that the recipient is not intent upon (at a social gathering, for example), and therefore, not facing. As the sound S enters the first opening 506a, a waveform of a particular frequency is transmitted within the lumen 504. This waveform is depicted by the solid line 514. Since the separation distance d and opening width w have been not optimized for frequencies that enter from a side of the recipient, the sound entering the second opening 506b results in a waveform of an identical frequency, but that is out of phase with the waveform 514. This out of phase waveform is depicted by dashed line 516. The resulting destructive interference between these two waveforms 514, 516 cancel each other out and no sound is received at the microphone. A processor disposed within an associated auditory prosthesis may also ignore or otherwise process sound waves of identical frequencies that are out of phase, but that do not cancel each other out.

Figure 8:
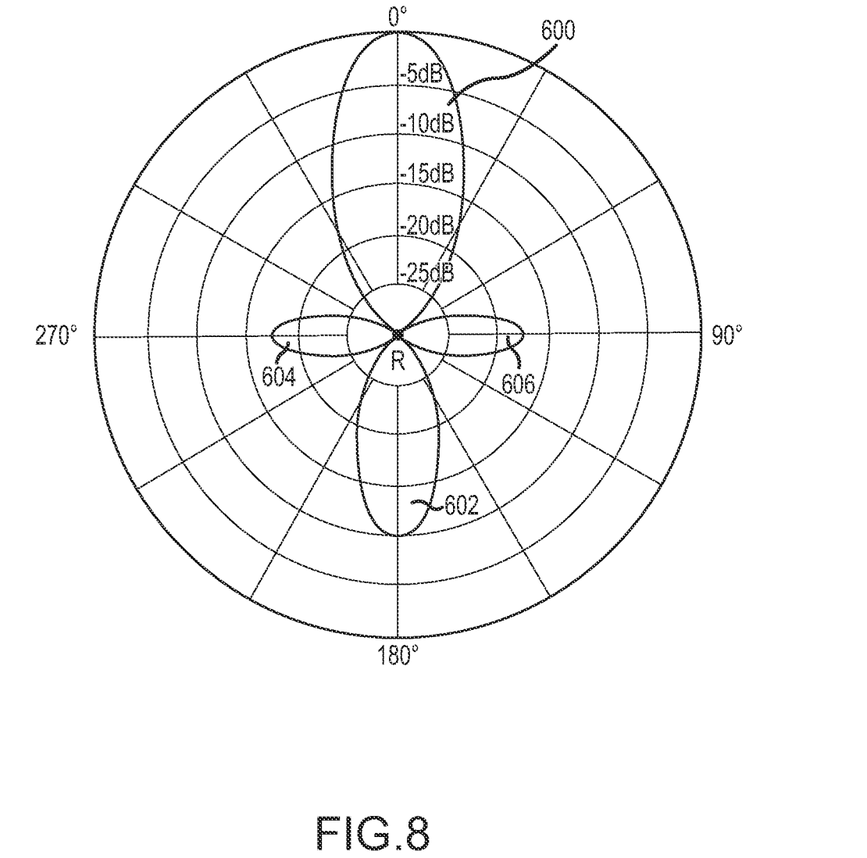
FIG. 8 is a polar plot graph of sounds received by an auditory prosthesis.

FIG. 8 depicts a polar plot graph of sound frequencies received by a recipient of an auditory prosthesis. The recipient R is located at the center of the graph and facing forward towards front lobe 600. A rear lobe 602 is located behind the recipient and side lobes 604, 606 are located to the sides of the recipient. The distance from the recipient to the outer edge of each lobe is indicative of the amplitude of sound from that particular direction. It has been determined that sounds from the front lobe 600 are the most desirable, since the recipient R typically focuses on sounds (e.g., speech) from a forward direction. Accordingly, more openings optimized to a predetermined desirable frequency will further reduce the size of the side lobes 604, 606. Thus, more destructive interference will be caused within the inlet tube for sounds coming from the sides.

Figure 9A:
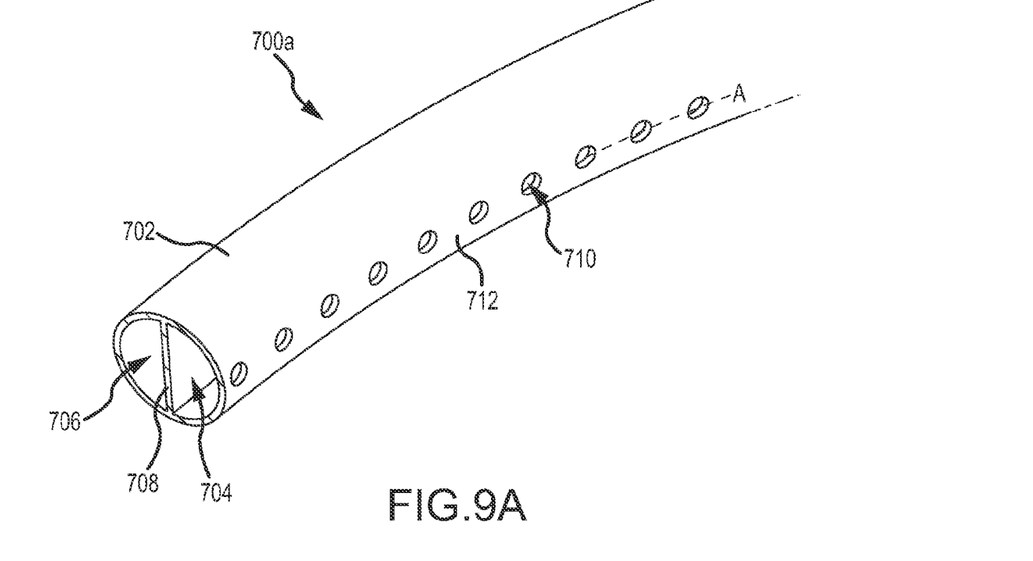
FIGS. 9A and 9B are schematic perspective views of embodiments of tubes utilized with auditory prostheses.
Figure 9B:
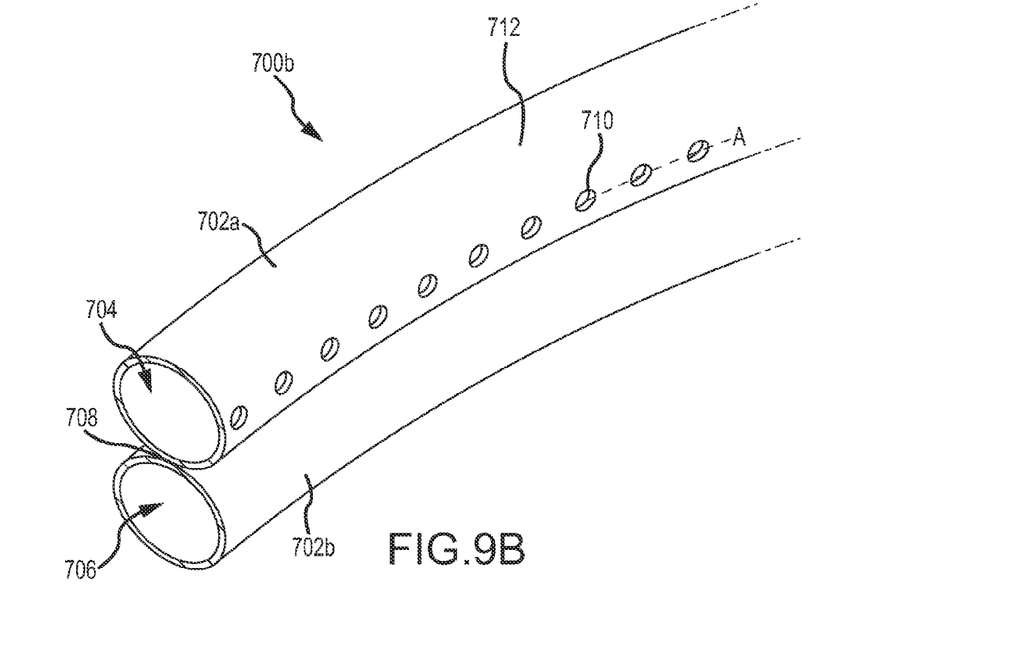

FIGS. 9A and 9B depict embodiments of earhooks 700 that can be utilized with certain embodiments of auditory prostheses depicted herein, namely, those that utilize a speaker in the prosthesis housing (as depicted, for example, in FIG. 4). In FIG. 9A, the earhook 700a is formed from an elongate annular body 702. The body 702 defines two discrete tubes, an inlet tube 704 and an outlet tube 706. The tubes 704, 706 are separated by a septum 708. A plurality of openings 710 are defined by an outer surface 712 along the inlet tube 704 portion of the member 702. Thus, sound enters the openings 710, is received and processed in the hearing device, and outputted through the outlet tube 706. In FIG. 9B, the earhook 700b is formed from two elongate bodies 702a, 702b. The body 702a defines an inlet tube 704, while the body 702b defines an outlet tube 706. The bodies 702a, 702b are joined at tangents thereof, thus forming a septum 708. Of course, in other embodiments, the bodies 702a, 702b can be discrete from each other. A plurality of openings 710 are defined by the outer surface 712 along the body 702a. In both embodiments, the openings 710 are aligned along an axis A. In other embodiments, the openings can be positioned along multiple axes, disposed randomly along the body, or otherwise oriented as required or desired for a particular application. Certain embodiments of auditory prostheses utilize an earhook as well as a discrete tube that is configured with openings as depicted in FIGS. 9B and 9B.

Figure 10:
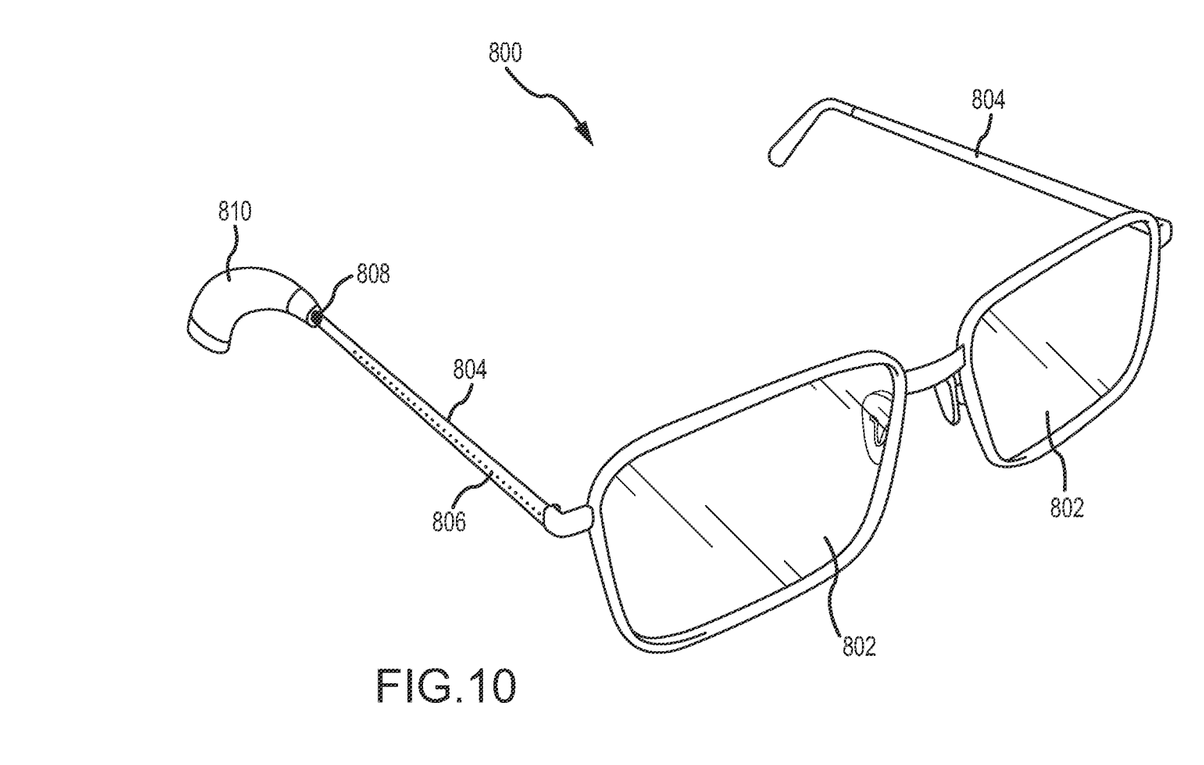
FIG. 10 is a schematic perspective view of an accessory incorporating an auditory prosthesis.

FIG. 10 is a schematic perspective view of an accessory 800 incorporating an auditory prosthesis. The accessory 800 is a pair of eye glasses that include lenses 802 and armatures 804. One or both of the armatures 804 can define a lumen and a plurality of openings 806. Sound is directed as described above to a microphone 808 disposed proximate an end of one of the armatures 804. An auditory prosthesis 810 can be removably or fixedly secured to that end of the armature 804. Received sound is processed as described herein and delivered to a recipient as a stimulus. Other types of accessories that can incorporate the technologies described herein include wearable computers having head-mounted displays. Such devices have form factors similar to eye glasses and can utilize bone conduction devices to transmit sounds to a recipient.

Figure 11:
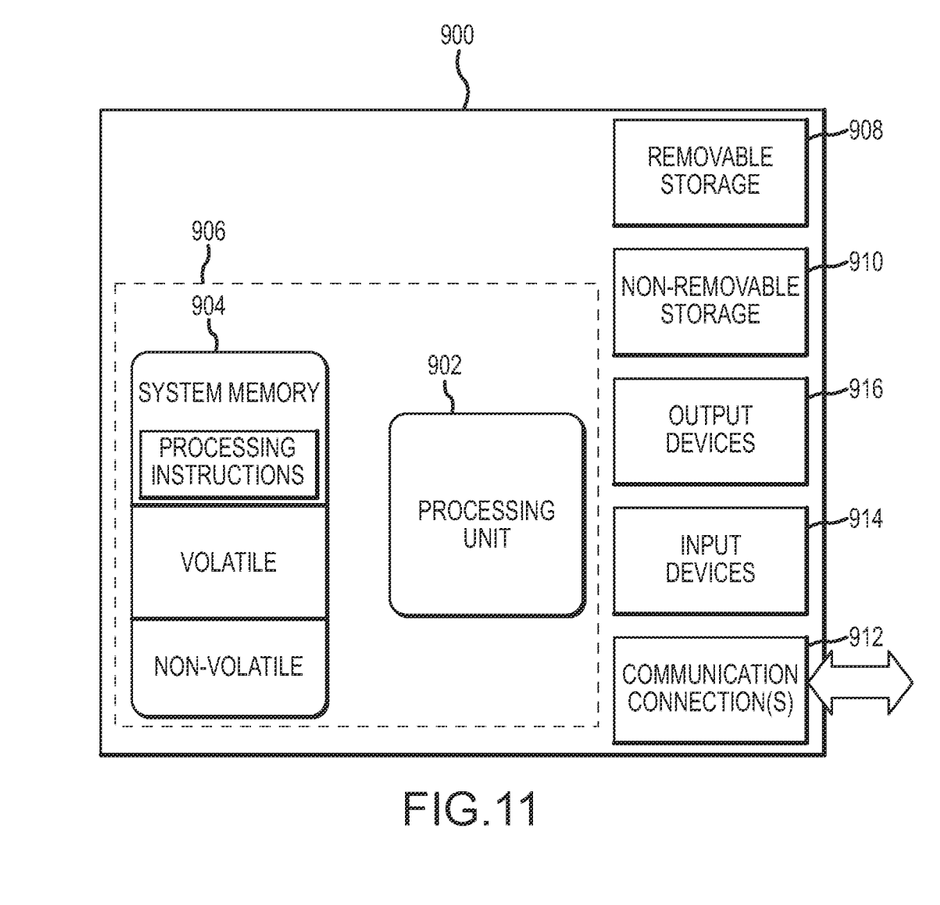
FIG. 11 illustrates one embodiment of a suitable operating environment in which one or more of the present embodiments can be implemented.

FIG. 11 illustrates one embodiment of a suitable operating environment 900 in which one or more of the present embodiments can be implemented. This is only one example of a suitable operating environment and is not intended to suggest any limitation as to the scope of use or functionality. Embodiments of the operating environment 900 can be housed in the auditory prostheses disclosed herein or a unit communicatively coupled to an auditory prosthesis, for example, in a behind-the-ear device 102, such as depicted in FIG. 1.

In its most basic configuration, operating environment 900 typically includes at least one processing unit 902 and memory 904. Depending on the exact configuration and type of computing device, memory 904 (storing, among other things, instructions to perform process the signals as described herein) can be volatile (such as RAM), non-volatile (such as ROM, flash memory, etc.), or some combination of the two. This most basic configuration is illustrated in FIG. 11 by line 906. Further, environment 900 can also include storage devices (removable, 908, and/or non-removable, 910) including, but not limited to, magnetic or optical disks or tape. Similarly, environment 900 can also have input device(s) 914 such as touch screens, buttons, dials, voice input, etc., and/or output device(s) 916 such as a display, speakers, etc. Also included in the environment can be one or more communication connections, 912, such as LAN, WAN, point to point, Bluetooth, RF, etc.

Operating environment 900 typically includes at least some form of computer readable media. Computer readable media can be any available media that can be accessed by processing unit 902 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

In some embodiments, the components described herein comprise such modules or instructions executable by computer system 900 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 900 is part of a network that stores data in remote storage media for use by the computer system 900.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An auditory prosthesis comprising:
a housing;
a microphone disposed in the housing;
a microphone inlet defined by the housing for receiving a sound; and
an inlet tube comprising a first open end, wherein the first open end is connected to the housing so as to substantially surround the microphone inlet, and wherein the inlet tube defines at least one opening disposed along an outer surface of the inlet tube.

2. The auditory prosthesis of claim 1, further comprising:
a processor operatively coupled to the microphone for converting the received sound into an output signal; and
a stimulation element operatively coupled to the processor, wherein the stimulation element receives the output signal from the processor and transmits to a recipient a stimulus based at least in part on the output signal.

3. The auditory prosthesis of claim 1, further comprising:
an insert; and
an outlet tube connecting the insert to the housing, wherein the stimulation element is disposed in at least one of the auditory prosthesis and the insert.

4. The auditory prosthesis of claim 3, wherein the stimulation element comprises a first stimulation element and a second stimulation element, wherein the second stimulation element is disposed in the insert.

5. The auditory prosthesis of claim 4, wherein the first stimulation element comprises at least one of an electrode array and a vibration device.

6. The auditory prosthesis of claim 5, wherein the first stimulation element is the electrode array and the stimulus stimulates at least one of the auditory nerve and a portion of the cochlea.

7. The auditory prosthesis of claim 6, wherein the second stimulation element comprises a speaker and the stimulus comprises an output sound.

8. The auditory prosthesis of claim 2, wherein the stimulation element is disposed in the housing.

9. The auditory prosthesis of claim 8, wherein stimulation element comprises an electrode array and the stimulus stimulates at least one of the auditory nerve and a portion of the cochlea.

10. The auditory prosthesis of claim 8, wherein the stimulation element comprises at least one of a vibration device to transmit a vibration stimulation, an electrode array to transmit an electrical stimulation, and an acoustic device to transmit an acoustic stimulation.

11. An auditory prosthesis comprising:
a wearable housing adapted to be located behind an ear of a recipient;
a microphone disposed within the wearable housing;
a tube defining at least one opening along at least a portion of the length of the tube, wherein the tube is configured to conform to a portion of an ear of a recipient, and wherein the tube terminates at an inlet to the microphone, wherein the auditory prosthesis comprises at least one of a bone conduction auditory prosthesis and a cochlear implant.

12. The auditory prosthesis of claim 11, further comprising an insert adapted to deliver an output sound to a recipient, wherein the tube connects the insert to the wearable housing.

13. The auditory prosthesis of claim 12, further comprising a stimulation element.

14. The auditory prosthesis of claim 13, wherein the stimulation element comprises a speaker disposed within the insert, wherein the speaker is electrically coupled to the wearable housing.

15. The auditory prosthesis of claim 13, wherein the stimulation element comprises a speaker disposed within the wearable housing.

16. The auditory prosthesis of claim 13, wherein the stimulation element comprises at least one of an electrode array and a vibration element.

17. The auditory prosthesis of claim 11, wherein the auditory prosthesis further comprises an acoustic hearing aid.

18. An auditory prosthesis comprising:
a microphone inlet;
a microphone in communication with the microphone inlet; and
an inlet tube comprising an outer wall defining a lumen, a first opening through the outer wall, and a second opening through the outer wall, wherein the inlet tube terminates at the microphone inlet, and wherein the first opening and the second opening are separated by a distance such that a sound having a predetermined frequency and passing through both the first opening and the second opening is transmitted in phase within the tube.

19. The auditory prosthesis of claim 18, wherein the lumen transmits to the microphone a sound received via both the first opening and the second opening.

20. The auditory prosthesis of claim 18, wherein the predetermined frequency is in a range of about 500 Hz to about 6000 Hz.

21. The auditory prosthesis of claim 18, wherein the predetermined frequency is in a range of about 1000 Hz to about 4000 Hz.

22. The auditory prosthesis of claim 18, further comprising:
an insert connected to the inlet tube; and
a stimulation element disposed in at least one of the insert and the auditory prosthesis.

23. The auditory prosthesis of claim 22, wherein the stimulation element is disposed within the auditory prosthesis.

24. The auditory prosthesis of claim 23, further comprising an outlet tube, wherein the inlet tube is connected to the outlet tube at a septum.

25. The auditory prosthesis of claim 18, wherein at least one of the plurality of openings is at least partially covered with a membrane.

26. An apparatus comprising:
a lens;
an armature connected to the lens, wherein the armature is configured to enable the lens to be worn on a recipient, and wherein the armature defines a plurality of openings and a hollow lumen in communication with the plurality of openings;
a microphone located proximate an end of the lumen;
an auditory prosthesis adapted to be secured to the armature proximate the microphone, wherein the auditory prosthesis comprises a bone conduction device.

27. The apparatus of claim 26, further comprising:
an auditory prosthesis secured to the armature, wherein the microphone is disposed within the auditory prosthesis.

28. The apparatus of claim 26, wherein the apparatus is a pair of eyeglasses.

* * * * *